United States Patent
Mullally

(10) Patent No.: US 11,944,458 B2
(45) Date of Patent: Apr. 2, 2024

(54) BREAST SECUREMENT DEVICES

(71) Applicant: Hologic, Inc., Marlborough, MA (US)

(72) Inventor: James Mullally, New Fairfield, CT (US)

(73) Assignee: Hologic, Inc., Marlborough, MA (US)

( * ) Notice: Subject to any disclaimer, the term of this patent is extended or adjusted under 35 U.S.C. 154(b) by 1083 days.

(21) Appl. No.: 16/577,643

(22) Filed: Sep. 20, 2019

(65) Prior Publication Data

US 2020/0093440 A1 Mar. 26, 2020

Related U.S. Application Data

(60) Provisional application No. 62/734,820, filed on Sep. 21, 2018.

(51) Int. Cl.
| | | |
|---|---|---|
| *A61B 6/04* | (2006.01) | |
| *A61B 5/00* | (2006.01) | |
| *A61B 6/00* | (2006.01) | |
| *A61B 8/00* | (2006.01) | |
| A61B 5/055 | (2006.01) | |
| A61B 6/50 | (2024.01) | |
| A61B 8/08 | (2006.01) | |

(52) U.S. Cl.
CPC ............ *A61B 5/708* (2013.01); *A61B 6/0414* (2013.01); *A61B 8/403* (2013.01); A61B 5/055 (2013.01); A61B 6/502 (2013.01); A61B 8/0825 (2013.01)

(58) Field of Classification Search
None
See application file for complete search history.

(56) References Cited

U.S. PATENT DOCUMENTS

| | | | | |
|---|---|---|---|---|
| 7,489,761 | B2* | 2/2009 | Defreitas | A61B 6/0414 378/208 |
| 9,901,320 | B2* | 2/2018 | DeFreitas | A61B 6/12 |
| 2005/0008117 | A1* | 1/2005 | Livingston | A61B 6/0414 378/37 |
| 2007/0234478 | A1* | 10/2007 | Baker | A61B 8/40 5/630 |
| 2012/0150034 | A1* | 6/2012 | DeFreitas | A61B 8/483 250/363.04 |
| 2013/0129039 | A1* | 5/2013 | DeFreitas | A61B 6/025 378/208 |
| 2020/0359974 | A1* | 11/2020 | Defreitas | A61B 6/0414 |

* cited by examiner

*Primary Examiner* — Jonathan Cwern
(74) *Attorney, Agent, or Firm* — Merchant & Gould P.C.

(57) ABSTRACT

Breast securement devices for imaging systems are provided. The securement device can include a breast tray configured to support a patient's breast. In one example, one or more walls extend from the breast tray to receive the patient's breast. In another example, a pair of arms pivotably extend at least partially over the breast tray to receive the patient's breast therebetween. In still another example, a membrane covers the breast tray and the patient's breast and selectively couples to the breast tray via a suction force. In yet another example, a paddle includes a plurality of flexible fingers that contour to the patient's breast, or includes an array of pins that independently slide within of the paddle and contour to the patient's breast, or includes a bladder having non-Newtonian fluid. Additionally or alternatively, a sling may receive the patient's breast and support the breast from below.

18 Claims, 9 Drawing Sheets

BREAST SECUREMENT DEVICES

CROSS-REFERENCE TO RELATED APPLICATIONS

This application claims priority to and the benefit of U.S. Provisional Patent Application No. 62/734,820, filed Sep. 21, 2018, the disclosure of which is hereby incorporated by reference herein in its entirety.

BACKGROUND

Breast securement during medical imaging (e.g., screening and diagnostic imaging procedures) serves a number of purposes. For example, it substantially stabilizes the breast during the imaging procedures, and thereby, reduces breast movement and image blurring. Additionally, optimal breast securement brings breast tissue out from the chest wall into the imaging field, and thus, enables more tissue imaging.

Some known breast securement methods include compressing and immobilizing the patient's breast for mammography, tomosynthesis, and/or computer tomography (CT) imaging. These systems generally use a movable, rigid, radiolucent compression paddle. The patient's breast is placed in an imaging area on a breast support platform that typically is flat, and the paddle then compresses the breast, usually while a technologist or other health professional is holding the breast in place. The technologist may also manipulate the breast to try to get proper tissue coverage in the image field.

One known challenge in breast stabilization is the discomfort the patient may feel when the breast is secured, which must be done with sufficient force to stabilize the breast. Discomfort may potentially cause the patient to move, which negatively impacts image quality. Discomfort may also potentially dissuade patients from getting screened for breast cancer. Another known challenge is to ensure that the imaged field includes the desired amount of breast tissue as stabilization may push breast tissue towards the patient's chest wall. Furthermore, the breast securement devices need to reduce or eliminate image artifacts being formed in the image.

SUMMARY

In one aspect, the technology relates to a breast securement device for an imaging system, the securement device including: a breast tray configured to support a patient's breast; and one or more walls extending from the breast tray and configured to receive at least a portion of the patient's breast. In an example, the one or more walls are adjustable on the breast tray. In another example, the one or more walls extend at an angle relative to the breast tray. In still another example, the breast tray includes a curved section disposed proximate the one or more walls. In yet another example, the one or more walls are substantially U-shaped and at least partially define a perimeter of the patient's breast while supported on the breast tray. In an example, the one or more walls are formed from a foam-based material.

In another aspect, the technology relates to a breast securement device for an imaging system, the breast securement device including: a support structure; a breast tray coupled to the support structure and configured to support a patient's breast; and a pair of arms pivotably connected to the support structure and extending at least partially over the breast tray, wherein the pair of arms are configured to receive at least a portion of the patient's breast therebetween. In an example, each arm of the pair of arms are angularly moveable relative to the support structure. In another example, each arm of the pair of arms includes a padded surface. In still another example, each arm of the pair of arms lock in place.

In still another aspect, the technology relates to a breast securement device for an imaging system, the breast securement device including: a support structure; and a sling coupled to the support structure and configured to receive at least a portion of the patient's breast and support the breast from below. In an example, the sling is formed from a fabric-based material. In another example, the sling is moveable along the support structure.

In yet another aspect, the technology relates to a breast securement device for an imaging system, the breast securement device including: a breast tray configured to support a patient's breast; a membrane configured to cover at least a portion of the breast tray and the patient's breast; and a vacuum system that when operated, selectively couples the membrane to the breast tray via a suction force. In an example, the breast tray includes a stabilization surface that has a plurality of holes for generating the suction force on the membrane. In another example, a vacuum chamber is defined at least partially within the breast tray. In still another example, the device further includes a cover between the patient's breast and the breast tray.

In another aspect, the technology relates to a breast securement device for an imaging system, the breast securement device including: a breast tray configured to support a patient's breast; and a paddle configured to move towards the breast tray and contact at least a portion of the patient's breast, wherein the paddle includes a plurality of flexible fingers configured to contour to the patient's breast. In an example, the plurality of flexible fingers are spaced apart from one another. In another example, the device further includes a membrane coupled between each of the plurality of flexible fingers. In still another example, the membrane includes a mesh, a fabric, a flexible plastic, and/or a bladder. In yet another example, the bladder is at least partially filled with a liquid or a gel-based material.

In still another aspect, the technology relates to a breast securement device for an imaging system, the breast securement device including: a breast tray configured to support a patient's breast; and a paddle configured to move towards the breast tray and contact at least a portion of the patient's breast, wherein the paddle includes an array of pins configured to independently slide within the paddle and contour to the patient's breast. In an example, each pin in the array of pins includes a fiber optic pin. In another example, each pin in the array of pins includes a radiolucent plastic. In still another example, the array of pins slide in a direction that is substantially similar to a direction of movement of the paddle. In yet another example, the array of pins create a relief of the patient's breast when the breast is received within the paddle.

In yet another aspect, the technology relates to a breast securement device for an imaging system, the breast securement device including: a bladder positionable adjacent to at least a portion of the patient's breast; and a non-Newtonian fluid disposed within the bladder, wherein upon an application of a stress, the non-Newtonian fluid increases in viscosity to stabilize the patient's breast. In an example, the device further includes an ultrasound generator configured to apply stress towards the non-Newtonian fluid. In another example, the bladder is coupled to a paddle. In still another example, the non-Newtonian fluid is substantially radiolucent.

DETAILED DESCRIPTION

Figure 1A:
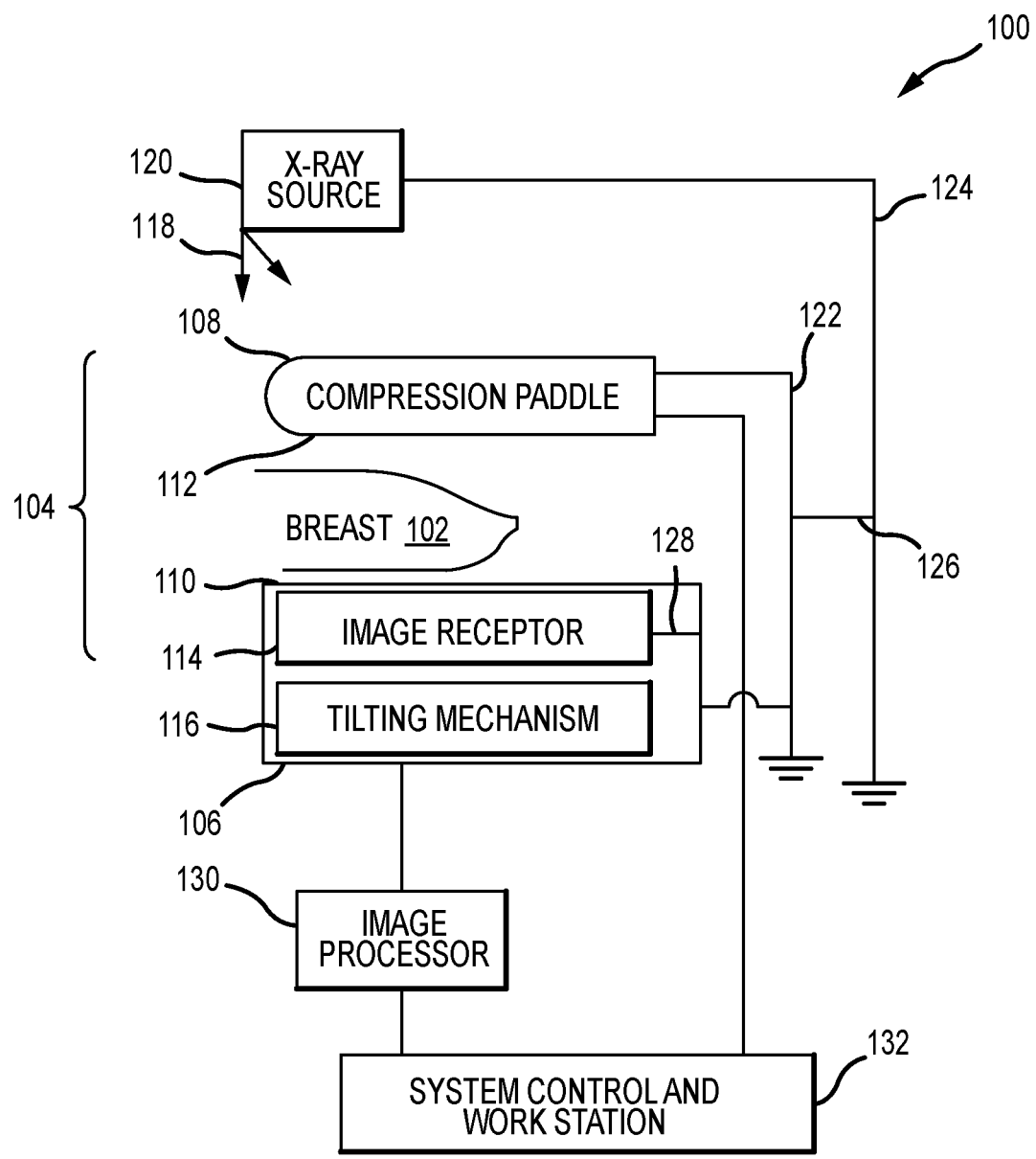
FIG. 1A is a schematic view of an exemplary imaging system.
Figure 1B:
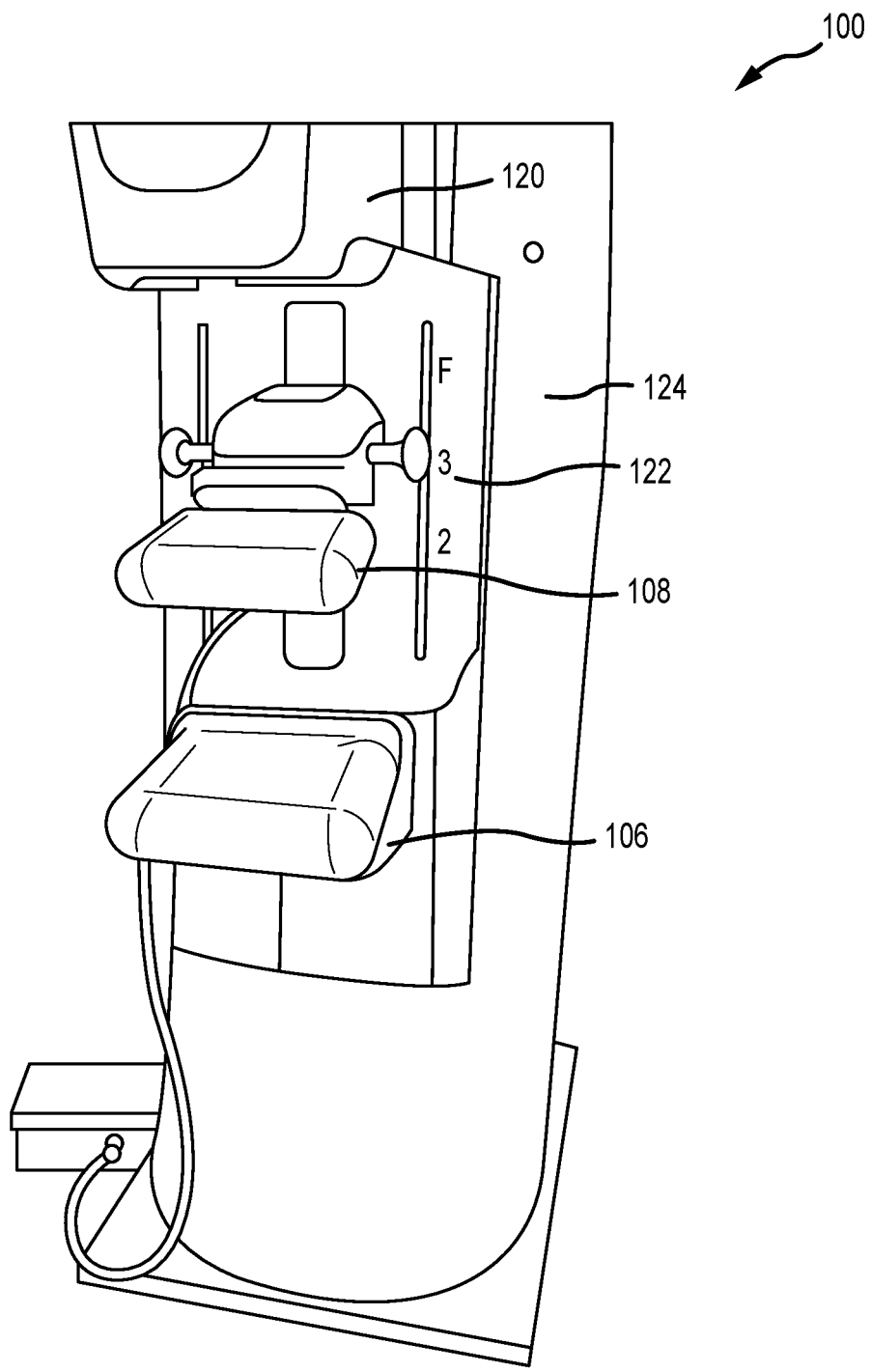
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 is configured to compress a patient's breast 102 for x-ray imaging via a breast compression system 104. In the example, the compression system 104 includes a breast support platform 106 and a moveable compression paddle 108. The breast support platform 106 and the compression paddle 108 each have a compression surface 110 and 112, respectively, with the compression surface 112 configured to move towards the support platform 106 to compress the breast 102 therebetween. In known systems, the compression surfaces 110, 112 are exposed so as to directly contact the breast 102. The support platform 106 also houses an image receptor 114 and, optionally, a tilting mechanism 116. The compression system 104 is in a path of an imaging x-ray beam 118 emanating from an x-ray source 120, such that the x-ray beam 118 impinges on the image receptor 114.

The compression system 104 is supported on a first support arm 122 and the x-ray source 120 is supported on a second support arm, also referred to as a tube arm 124. For mammography, support arms 122 and 124 can rotate as a unit about an axis 126 between different imaging orientations such as cranial-caudal (CC) and mediolateral oblique (MLO) views, so that the imaging system 100 can take a mammogram projection image at each orientation. In operation, the image receptor 114 remains in place relative to the support platform 106 while an image is taken. The compression system 104 releases the breast 102 for movement of support arms 122, 124 to a different imaging orientation. For tomosynthesis, the support arm 122 stays in place, with the breast 102 compressed and remaining in place, while at least the tube arm 124 rotates the x-ray source 120 relative to the compression system 104 and the compressed breast 102 about the axis 126. The imaging system 100 takes plural tomosynthesis projection images of the breast 102 at respective angles of the x-ray beam 118 relative to the breast 102. As such, the compression system 104 and tube arm 124 may be rotated discrete from each other, unless matched rotation is required or desired for an imaging procedure.

Concurrently and optionally, the image receptor 114 may be tilted relative to the breast support platform 106 and coordinated with the rotation of the second support arm 124. The tilting can be through the same angle as the rotation of the x-ray source 120, but may also be through a different angle selected such that the x-ray beam 118 remains substantially in the same position on the image receptor 114 for each of the plural images. The tilting can be about an axis 128, which can but need not be in the image plane of the image receptor 114. The tilting mechanism 116 that is coupled to the image receptor 114 can drive the image receptor 114 in a tilting motion. For tomosynthesis imaging and/or CT imaging, the breast support platform 106 can be horizontal or can be at an angle to the horizontal, e.g., at an orientation similar to that for conventional MLO imaging in mammography. The imaging system 100 can be solely a mammography system, a CT system, or solely a tomosynthesis system, or a "combo" system that can perform multiple forms of imaging. An example of one combo system has been offered by the assignee hereof under the trade name Selenia Dimensions. For CT systems, the breast 102 may be compressed in the compression system 104, however, the image receptor 114 is remote from the support platform 106 and rotates with the x-ray source 120 and relative to the compression system 104.

When the system is operated, the image receptor 114 produces imaging information in response to illumination by the imaging x-ray beam 118, and supplies it to an image processor 130 for processing and generating breast x-ray images. A system control and work station unit 132, including software, controls the operation of the system and interacts with the operator to receive commands and deliver information including processed-ray images.

While the imaging system 100 described above is an x-ray imaging system, it should be appreciated that the imaging system 100 can alternatively or additionally be any other type of imaging system as required or desired. In one example, the imaging system 100 may be an ultrasound imaging system that generates ultrasonic images of the patient's breast 102 via sound waves. In another example, the imaging system 100 may be a magnetic resonance imaging (MRI) system that generates images of the patient's breast 102 via radio waves. Other imaging systems known in breast diagnosis and screening procedures are also contemplated herein. In each example of the imaging system 100, it is desirable to sufficiently secure the patient's breast 102 so as to reduce breast movement and image blurring. Shaping the patient's breast 102 may also be desirable so as to increase imaging procedure efficiencies. Additionally, breast securement and/or shaping can bring breast tissue out from the chest wall into the imaging field, and thus, enabling greater tissue imaging.

One challenge in each example of the imaging system 100 (e.g., mammography, tomosynthesis, CT, ultrasound, MM, etc.) is how to efficiently secure the breast 102 for the desired or required imaging. In each example, it is desirable to sufficiently secure the patient's breast 102 so as to reduce breast movement and image blurring during image acquisition. Additionally, breast securement can shape the breast 102 while also bringing breast tissue out from the chest wall into the imaging field. Thus, breast stabilization and shaping enables more effective and efficient breast tissue imaging. Furthermore, breast securement increases patient comfort, which further reduces patient movement. Other benefits may also be realized by securing and stabilizing the patient's breast.

The technologies described herein relate to securement devices that are configured to stabilize the patient's breast 102 with respect to the imaging system 100, without requiring the compression pressure typical of that in the compression system 104 that is described above. Unlike the typical hard plastic compression paddles 108, the securement devices herein need not flatten the breast 102. Rather, the securement devices are used to stabilize and/or shape the patient's breast 102, not necessarily to effectuate full compression. Additionally, the securement devices may be used prior to full compression and flattening, for example, to adjust and/or position the patient's breast 102 within the compression system 104. Accordingly, as described herein, breast securing sufficiently stabilizes the patient's breast with respect to the imaging system 100 such that movement of the breast is restricted or eliminated. This breast securing and stabilization may not result in full compression and flattening, but may reduce or eliminate image blurring, while increasing the efficiency, comfort, and performance of the imaging procedure. Exemplary breast securement devices are described in further detail below.

The breast securement devices described herein are configured to couple to the imaging system to stabilize and/or shape the patient's breast with respect to the imaging system. As such, the patient's breast is restricted or prevented from moving during imaging procedures to reduce or eliminate image blurring, while increasing the efficiency, comfort, and performance of the imaging procedure. The breast securement devices are also substantially radiolucent and/or sonolucent to reduce image artifacts being formed in the image. In one aspect, the breast securement devices can include one or more walls that extend from a breast tray. For example, the walls can be positioned along the sides of the patient's breast, can be angled relative to the breast tray so as to substantially surround the patient's breast, and/or can be formed around a perimeter of the patient's breast. These walls receive and support the sides of the patient's breast and enable the patient's breast to be stabilized on the breast tray so that the breast does not move during imaging and the patient's comfort level is increased. Furthermore, the walls can enable the patient's breast to be more easily positioned within the imaging area of the imaging system by the technologist. In another aspect, a pair of substantially V-shaped arms may be used to stabilize and/or shape the patient's breast on a breast tray and increase patient comfort. These arms also receive and support the sides of the patient's breast to enable the patient's breast to be stabilized on the breast tray. Additionally, the arms can be selectively angularly rotated and locked in position so that when the breast tray is rotated into a MLO angled position, one arm can be used to support the patient's breast in the MLO angled and reduce breast sagging. By using walls and/or arms to secure the sides of the patient's breast, the top of the patient's breast is open to the imaging source and image artifacts are reduced or eliminated. Additionally or alternatively, by securing the sides of the patient's breast, the top of the patient's breast is open to other devices, such as a biopsy device.

In yet another aspect, the breast securement device can include a sling that stabilizes and/or shapes the patient's breast from below to restrict movement. The sling can be disposable to facilitate cleaning and/or be moveable to accommodate different patient heights and breast sizes. By supporting the breast from below, breast tissue can be pulled away from the chest wall and into the image area. Furthermore, the top of the patient's breast is open to the imaging source so that image artifacts are reduced or eliminated and is open to devices such as biopsy devices. In still another example, a vacuum system may be used to stabilize and/or shape the patient's breast and increase patient comfort. The vacuum system may be at least partially disposed within the breast tray and generate a suction force on a membrane that covers the patient's breast and the breast tray. As such, the patient's breast is secured between the membrane and the breast tray to increase imaging efficiencies. Furthermore, pinch points on the breast can be reduced or eliminated when compared to the compression system described above. The suction force can also pull breast tissue away from the chest wall and into the image area.

In a further aspect, the breast securement devices may be disposed on a paddle that contacts at least a portion of the patient's breast. These paddles, however, do not fully compress the patient's breast as described above, rather these paddles contour around the patient's breast to stabilize and/or shape the breast. For example, the paddle may include a plurality of flexible fingers that contour around the patient's breast. This contour restricts or eliminates movement of the patient's breast and increases imaging efficiencies and patient comfort. In another example, the paddle may include an array of pins that independently slide and contour around the patient's breast. The pins restrict or eliminate movement of the patient's breast and increases imaging efficiencies and patient comfort. In still another example, the paddle may include a bladder with a non-Newtonian fluid. With non-Newtonian fluid, when a stress is applied to the fluid, the fluid increases in viscosity to become more rigid and stiff so as to stabilize the patient's breast. However, when the stress is removed, the fluid returns to a sufficiently motile (e.g., low viscosity) state so that the bladder may easily contour around the patient's breast. All of these devices enable the stabilization and/or shaping the patient's breast for imaging, without requiring the compression pressure typical in breast imaging systems.

Figure 2A:
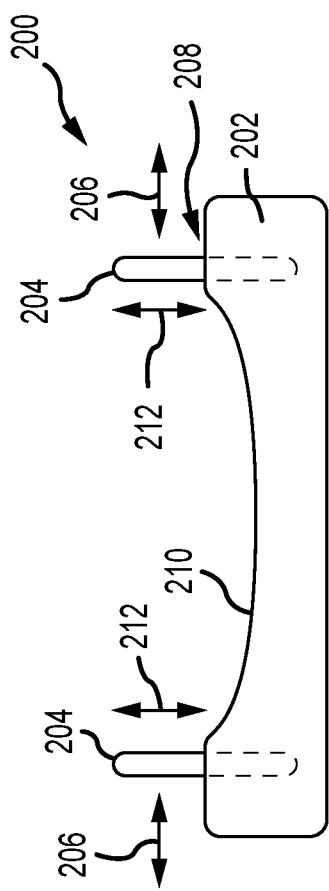
FIG. 2A is a schematic front view of an exemplary breast securement device.

FIG. 2A is a schematic front view of an exemplary breast securement device 200. The breast securement device 200 is configured to operationally couple to an imaging system (e.g., mammography, tomosynthesis, CT, ultrasound, MRI, etc.), such as the imaging system 100 described above in FIGS. 1A-1B, and stabilize and/or shape the patient's breast for image acquisitions. In the example, the breast securement device 200 includes a breast tray 202 configured to support a patient's breast. Additionally, one or more walls 204 extend from the breast tray 202 and are configured to receive at least a portion of the patient's breast. In the example, the walls 204 can be positioned on the right and/or left sides of the patient's breast and enable the breast to be secured on the breast tray 202. In some examples, a wall (not shown) may also extend substantially orthogonal to the nipple region of the patient's breast. The walls 204 facilitate stabilizing the patient's breast on the breast tray 202 so that the breast does not move during imaging and the patient's comfort level is increased. Furthermore, the walls 204 enable the patient's breast to be more easily positioned within the imaging area of the imaging system. For example, defining the imaging area on the breast tray 202 for the imaging technologist.

In some examples, the walls 204 are fixed to the breast tray 202 and can be moveably adjustable 206 along a stabilization surface 208 of the breast tray 202. This enables different breast sizes to be accommodated within the breast securement device 200. In other examples, the walls 204 can be selectively attached to the breast tray 202 at different locations to facilitate adjustment of the walls 204. Additionally or alternatively, the breast tray 202 may include a curved section 210 disposed proximate the one or more walls 204. The curved section 210 may further facilitate stabilizing and/or shaping the patient's breast on the breast tray 202. In other examples, the walls 204 may be adjustable 212 in height so as to accommodate different size breasts. In the example, the walls 204 may be substantially rigid so as to stabilize the patient's breast. In other examples, at least a portion of the wall 204 may be flexible as required or desired. In an aspect, the walls 204 may be formed from a foam-based material so that image artifacts are not formed and patient comfort is increased.

Figure 2B:
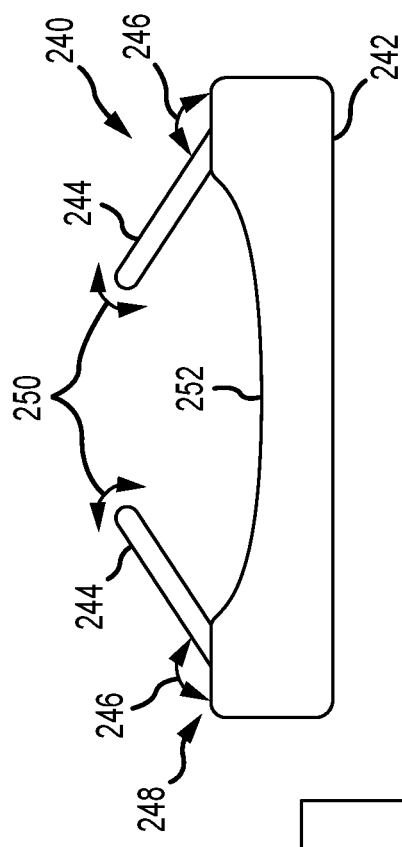
FIG. 2B is a schematic front view of another breast securement device.

FIG. 2B is a schematic front view of another breast securement device 240. Similar to the device described above in FIG. 2A, the breast securement device 240 is configured to operationally couple to an imaging system (e.g., mammography, tomosynthesis, CT, ultrasound, MRI, etc.) and stabilize and/or shape the patient's breast for image acquisitions. The breast securement device 240 includes a breast tray 242 configured to support a patient's breast. Additionally, one or more walls 244 extend from the breast tray 242 and are configured to receive at least a portion of the patient's breast. In this example, the walls 244 are positioned on the right and/or left sides of the patient's breast and extend at an angle 246 (e.g., obtuse angle) relative to a stabilization surface 248 of the breast tray 242. By angling the walls 244, the breast securement device 240 can extend further around the patient's breast to enable the stabilization of the patient's breast on the breast tray 242 so that the breast does not move during imaging and the patient's comfort level is increased.

In some examples, the walls 244 can be rotatably adjustable 250 relative to the stabilization surface 248 so that the angle 246 of the walls 244 is selectively positionable as required or desired. This enables the patient's breast to be more easily placed on the breast tray 242 and different breast sizes can be accommodated. Additionally or alternatively, the breast tray 242 may include a curved section 252 disposed proximate the one or more walls 244. The curved section 252 may further facilitate stabilizing and/or shaping the patient's breast on the breast tray 242. As described above, the walls 244 may be substantially rigid so as to stabilize the patient's breast. In other examples, at least a portion of the wall 244 may be flexible as required or desired. In an aspect, the walls 244 may be formed from a foam-based material so that image artifacts are not formed and patient comfort is increased.

Figure 2C:
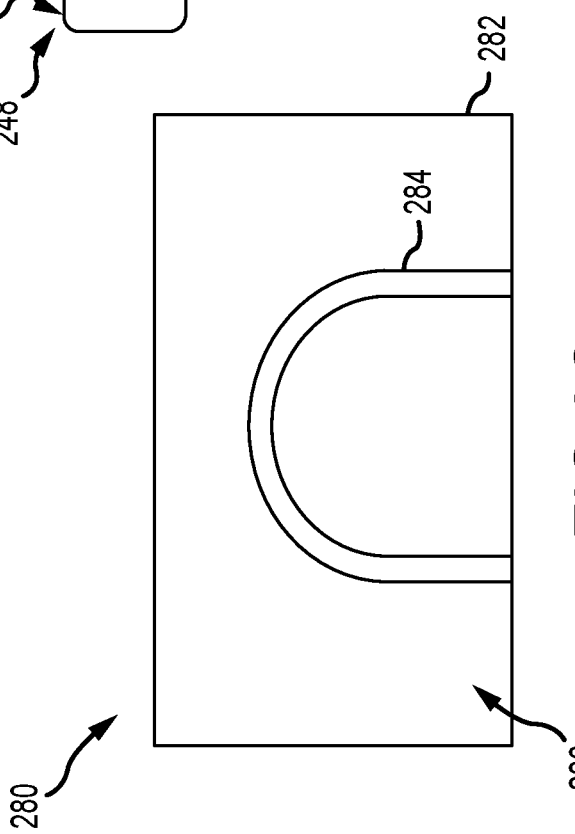
FIG. 2C is a schematic top view of another breast securement device.

FIG. 2C is a schematic top view of another breast securement device 280. Similar to the devices described above in FIGS. 2A and 2B, the breast securement device 280 is configured to operationally couple to an imaging system (e.g., mammography, tomosynthesis, CY, ultrasound, MRI, etc.) and stabilize and/or shape the patient's breast for image acquisitions. The breast securement device 280 includes a breast tray 282 configured to support a patient's breast. Additionally, a substantially U-shaped wall 284 is coupled to the breast tray 282 and is configured to receive at least a portion of the patient's breast. In this example, the wall 284 is shaped to at least partially define a perimeter of the patient's breast while supported on the breast tray 282. By using the wall 284 to define the perimeter of the patient's breast, the breast can be stabilized on the breast tray 282 so that the breast does not move during imaging and the patient's comfort level is increased. Furthermore, the wall 284 can enable the patient's breast to be more easily positioned within the imaging area of the imaging system. In other examples, the wall 284 can be selectively coupled to breast tray 282 (e.g., adhered) after the patient's breast is placed on the stabilization surface 286. In some examples, the wall 284 may be formed from a foam-based material and is coupled to a stabilization surface 286 of the breast tray 282.

In the examples described above in FIGS. 2A-2C, the breast tray is configured to support the patient's breast for imaging procedures. As such, the breast tray may correspond to the platform described in reference to FIGS. 1A and 1B. In other examples, the breast tray may correspond to the paddle described in reference to FIGS. 1A and 1B so that the walls extend from the paddle to facilitate stabilizing and/or shaping the patient's breast as required or desired between the platform and the paddle. Additionally or alternatively, the breast securement devices may be used to position and/or stabilize the patient's breast prior to compressing the breast as described above. In this example, the walls may be at least partially flexible so as to enable compression of the breast between the platform and the paddle.

Figure 3:
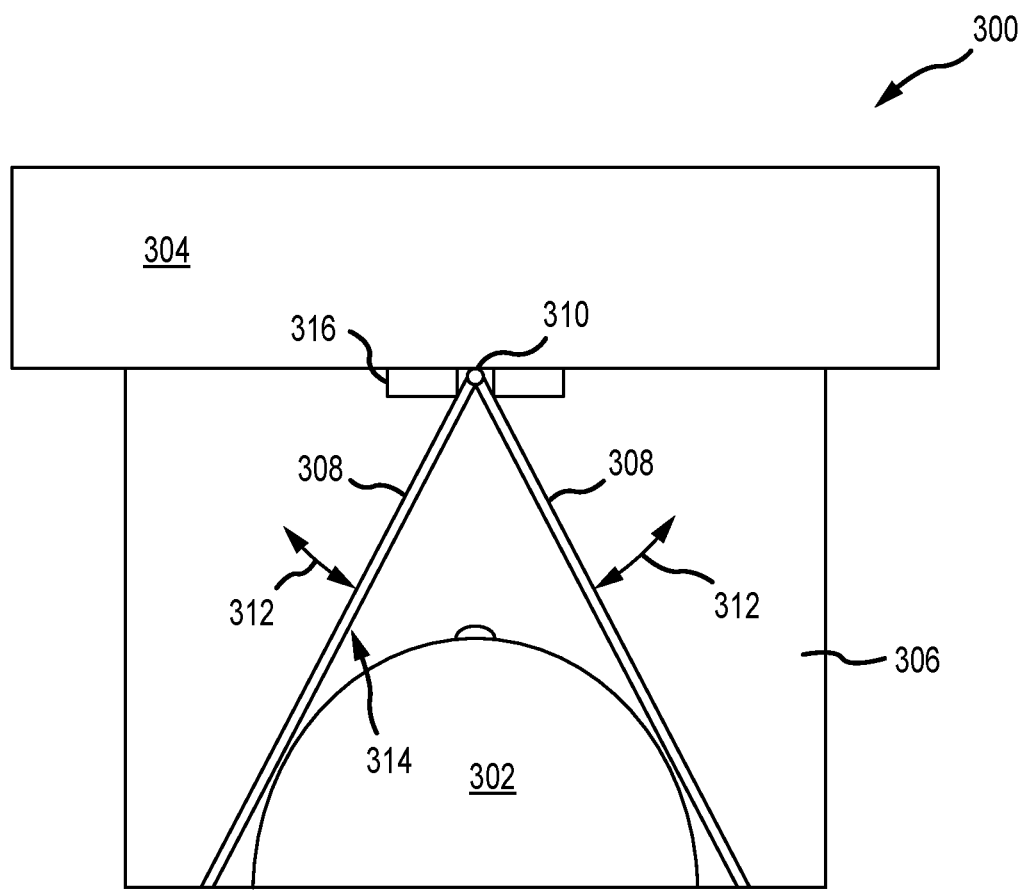
FIG. 3 is a schematic top view of another breast securement device.

FIG. 3 is a schematic top view of another breast securement device 300. The breast securement device 300 is configured to operationally couple to an imaging system (e.g., mammography, tomosynthesis, CT, ultrasound, MRI, etc.) and stabilize and/or shape a patient's breast 302 for image acquisitions. In this example, the breast securement device 300 includes a support structure 304 that supports a breast tray 306 and a pair of V-shaped arms 308. For example, the support structure 304 may be the support arm described in FIGS. 1A and 1B. The breast tray 306 is coupled to the support structure 304 and is configured to support the patient's breast 302. The arms 308 are pivotably connected to the support structure 304 at a pivot point 310. The arms 308 extend at least partially over the breast tray 306 and are configured to receive at least a portion of the patient's breast 302 therebetween. The arms 308 are substantially rigid and facilitate stabilizing the patient's breast 302 on the breast tray 306 so that the breast does not move during imaging and the patient's comfort level is increased. Furthermore, the arms 308 enables the patient's breast 302 to be more easily positioned within the imaging area of the imaging system.

In the example, each arm 308 is angularly moveable 312 relative to the support structure 304 and the breast tray 306. This enables different breast sizes to be accommodated within the breast securement device 300. For example, in order to secure the patient's breast, the technologist can position the breast on the breast tray 306 and then selectively move the arms 308 towards the right and/or left sides of the breast. By securing the patient's breast 302 along the right and/or left sides, one arm 308 can also be used to support the breast during MLO angled imaging and eliminate breast sagging. For example, in an MLO angle position, one arm 308 can be moved to the MLO position and used to support the patient's breast from underneath, and then once the breast is in place over the arm 308, the other arm 308 can be moved towards the patient's breast to stabilize the breast between the arms 308. This procedure and securement device 300 can reduce breast sagging during MLO angled imaging. To increase patient comfort, an inner surface of each arm 308 may include a padded surface 314. Additionally or alternatively, each arm 308 may include a locking mechanism 316 so that the arms 308 can be locked in place (e.g., selective angles) as required or desired.

The breast securement device 300 stabilizes the patient's breast 302 so that movement of the breast is reduced or eliminated for imaging procedures. Additionally or alternatively, the breast securement device 300 may be used to stabilize and/or position the patient's breast 302 prior to breast compression. In this example, the arms 308 can be disposed between the platform and the paddle. In other examples, the arms 308 may at least partially grip the patient's breast 302 so as to pull breast tissue away from the chest wall for image acquisition.

Figure 4:
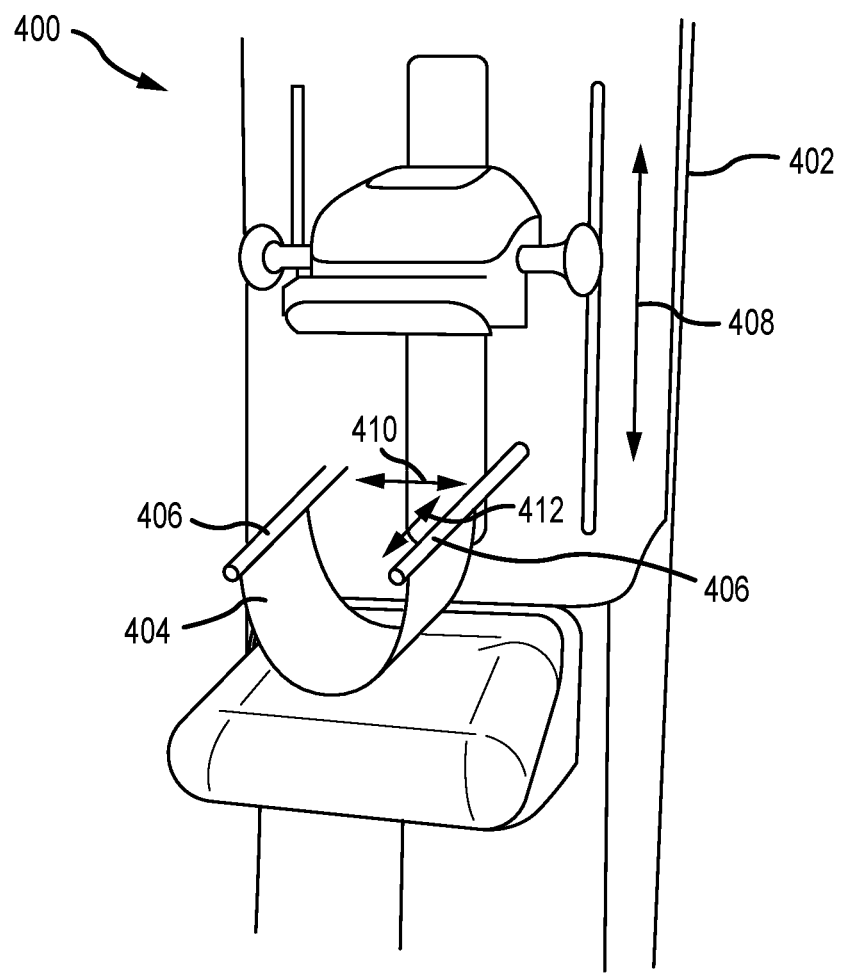
FIG. 4 is a schematic perspective view of another breast securement device.

FIG. 4 is a schematic perspective view of another breast securement device 400. The breast securement device 400 is configured to operationally couple to an imaging system (e.g., mammography, tomosynthesis, CT, ultrasound, MRI, etc.) and stabilize and/or shape a patient's breast for image acquisitions. In this example, the breast securement device 400 includes a support structure 402 and a sling 404 coupled to the support structure 402. For example, the support structure 402 may be the support arm described in FIGS. 1A and 1B. The sling 404 is configured to receive at least a portion of the patient's breast and support the breast from below so that the breast does not move during imaging and the patient's comfort level is increased. Furthermore, the sling 404 enables the patient's breast to be more easily positioned within the imaging area of the imaging system.

In the example, the breast securement device 400 may include a pair of support arms 406 that extend from the support structure 402. The support arms 406 are configured to receive at least a portion of the sling 404 so that the sling 404 is supported on the support structure 402. The arms 406 can be moveable 408 (e.g., up and down) along the support structure 402 so that the sling 404 can be positionable on the imaging system based on the height of the patient. The sling 404 can also removably attach to the arms 406 so that the sling 404 can be disposable and replaced for each patient procedure. In other examples, the sling 404 may be sanitizable and reusable as required or desired. The sling 404 may be formed from a fabric-based material so as to provide patient comfort and to reduce and/or eliminate image artifacts. In some examples, the arms 406 may be moveable 410 (e.g., left and right) so that different size breasts can be accommodated and/or to facilitate shaping the patient's breast as required or desired. The moveable 410 arms 406 may also be used to wrap the sling 404 at least partially around the patient's breast so as to further secure and stabilize the breast from undesirable movement.

The breast securement device 400 stabilizes the patient's breast so that movement of the breast is reduced or eliminated for imaging procedures. Additionally or alternatively, the breast securement device 400 may be used to stabilize and/or position the patient's breast prior to breast compression. In this example, the sling 404 can disposed between the platform and the paddle and used to lift the breast off of the platform prior to breast compression. In other examples, the arms 406 may also be moveable 412 (e.g., in and out) with respect to the support structure 402 so as to pull breast tissue away from the chest wall for image acquisition.

The breast securement devices described in FIGS. 2A-4, all either stabilize the patient's breast from the sides (e.g., the walls and the arms) or from below (e.g., the sling). As such, the top of the patient's breast is open for imaging sources and free from structure that generate image artifacts. Furthermore, because the top of the patient's breast is free from structure, other devices, such as biopsy devices, may have easier access to the patient's breast, while the breast is stabilized and restricted from movement.

Figure 5A:
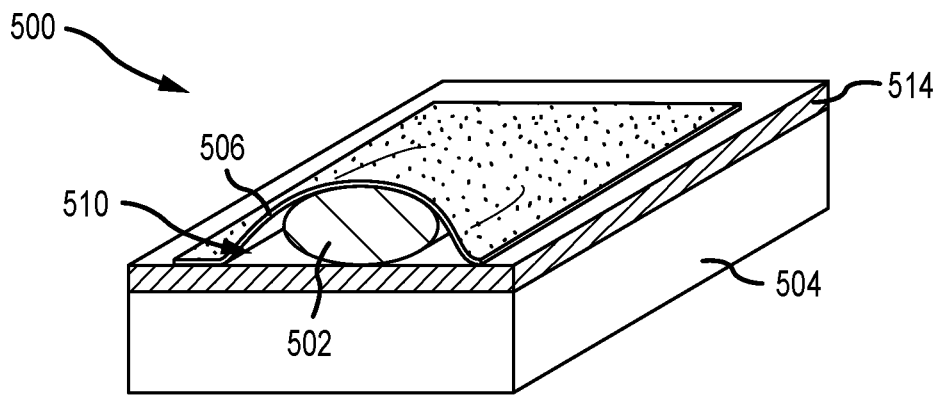
FIG. 5A is a perspective view of another breast securement device.
Figure 5B:
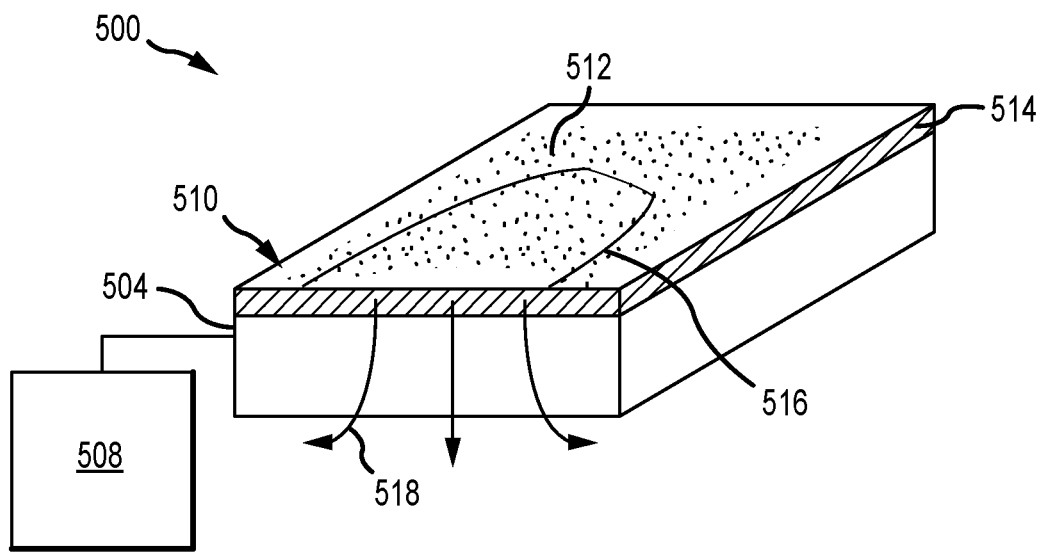
FIG. 5B is a schematic perspective view of the breast securement device of FIG. 5A.

FIG. 5A is a perspective view of another breast securement device 500. FIG. 5B is a schematic perspective view of the breast securement device 500. Referring concurrently to FIGS. 5A and 5B, the breast securement device 500 is configured to operationally couple to an imaging system (e.g., mammography, tomosynthesis, CT, ultrasound, MM, etc.) and stabilize and/or shape a patient's breast 502 for image acquisitions. In this example, the breast securement device 500 includes a breast tray 504 configured to support the patient's breast. A flexible membrane 506 is configured to cover at least a portion of the breast tray 504 and the patient's breast 502. The breast securement device 500 also includes a vacuum system 508 that when operated, selectively couples the membrane 506 to the breast tray 504 via a suction force. The suction force enables the patient's breast 502 to be stabilized and/or shaped on the breast tray 504 so that the breast does not move during imaging and the patient's comfort level is increased.

The breast tray 504 includes a stabilization surface 510 that has a plurality of holes 512 defined therein such that air can be vacuumed out from between the membrane 506 and the breast tray 504. A vacuum chamber 514 is defined at least partially within the breast tray 504 and adjacent the stabilization surface 510, which is utilized to vacuum out the air between the membrane 506 and the breast tray 504. In operation, the image technologist can place and position the patient's breast 502 on the stabilization surface 510. In some examples, a cover 516 may be placed between the patient's breast 502 and the breast tray 504 so that the holes 512 are covered and the breast tissue is not suctioned into the holes 512. A vacuum is then drawn through the vacuum chamber 514 such that air is drawn out 518 of the space between the membrane 506 and the breast tray 504 and a suction force is generated on the membrane 506 to stabilize the patient's breast 502. The membrane 506 may be disposable so as to increase cleaning efficiencies. In some examples, the holes 512 may be disposed outside of an image area (not shown) on the stabilization surface 510 so that image artifacts are reduced or eliminated during imaging. In other examples, the membrane 506 may be coupled to the breast try 504 such that the vacuum is applied directly to the membrane 506 and the stabilization surface 510 does not need to have any holes.

The breast securement device 500 stabilizes the patient's breast 502 so that movement of the breast is reduced or eliminated for imaging procedures. The breast securement device 500 can also pull breast tissue away from the chest wall for image acquisition by the suction force. By using the suction system 508, the suction force applied to the patient's breast 502 may be more easily controllable when compared to the rigid compression system described above in FIGS. 1A and 1B and breast tissue pinch points are reduced or eliminated. Additionally or alternatively, the breast securement device 500 may be used to stabilize and/or position the patient's breast 502 prior to breast compression. In this example, the membrane 506 can disposed between the platform and the paddle and used to position and/or adjust the patient's breast 502 prior to breast compression.

Figure 6:
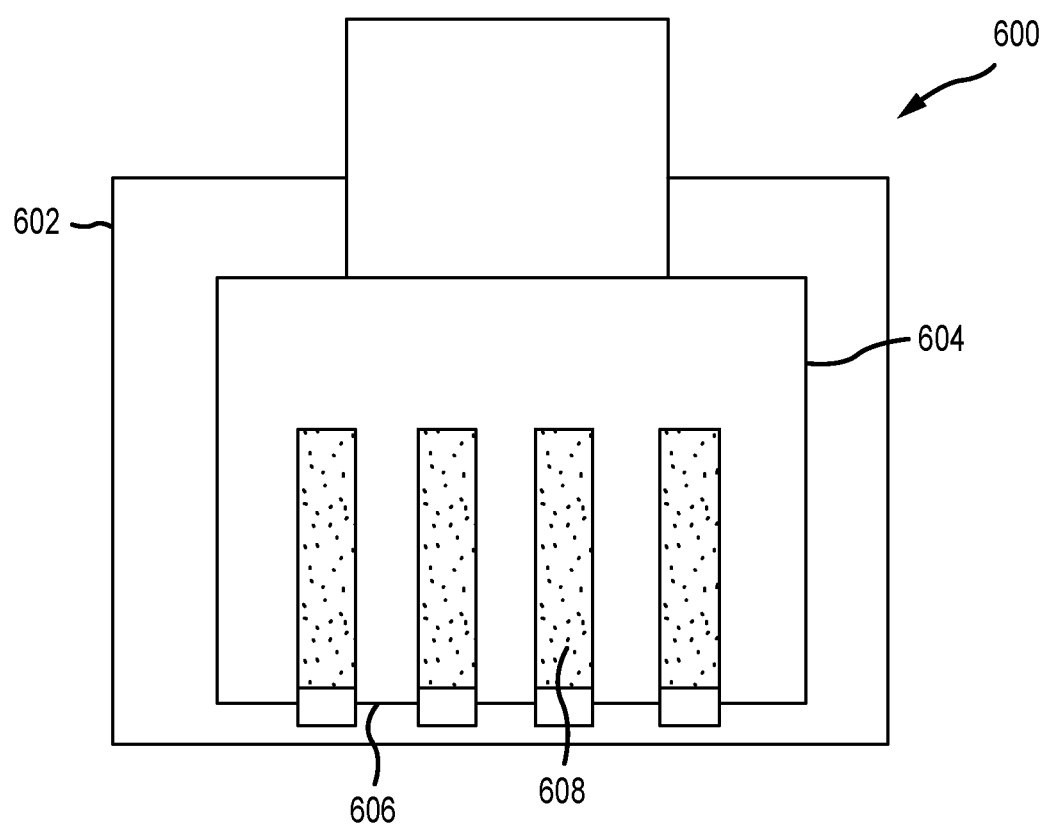
FIG. 6 is a schematic top view of another breast securement device.

FIG. 6 is a schematic top view of another breast securement device 600. The breast securement device 600 is configured to operationally couple to an imaging system (e.g., mammography, tomosynthesis, CT, ultrasound, MRI, etc.) and stabilize and/or shape a patient's breast for image acquisitions. In this example, the breast securement device 600 includes a breast tray 602 configured to support the patient's breast. A paddle 604 is positioned above the breast tray 602 and is configured to move towards the breast tray 602 and contact at least a portion of the patient's breast. The paddle 604 enables the patient's breast to be stabilized and/or shaped on the breast tray 602 so that the breast does not move during imaging and the patient's comfort level is increased.

In the example, the paddle 604 is substantially rigid and includes a plurality of flexible fingers 606 configured to contour at least partially around the patient's breast. The fingers 606 are spaced apart from one another so that the fingers 606 can independently move and flex around the patient's breast as required or desired. The fingers 606 extend towards the chest wall of the patient so that breast tissue may also be pulled away from the chest wall. In some examples, a membrane 608 may be coupled between each of the plurality of flexible fingers 606 to further reduce or eliminate breast movement and to increase patient comfort. The membrane 608 may be radiolucent and a mesh, a fabric, a flexible plastic, and/or a bladder. The bladder may be at least partially filled with a liquid or a gel-based material.

Figure 7:
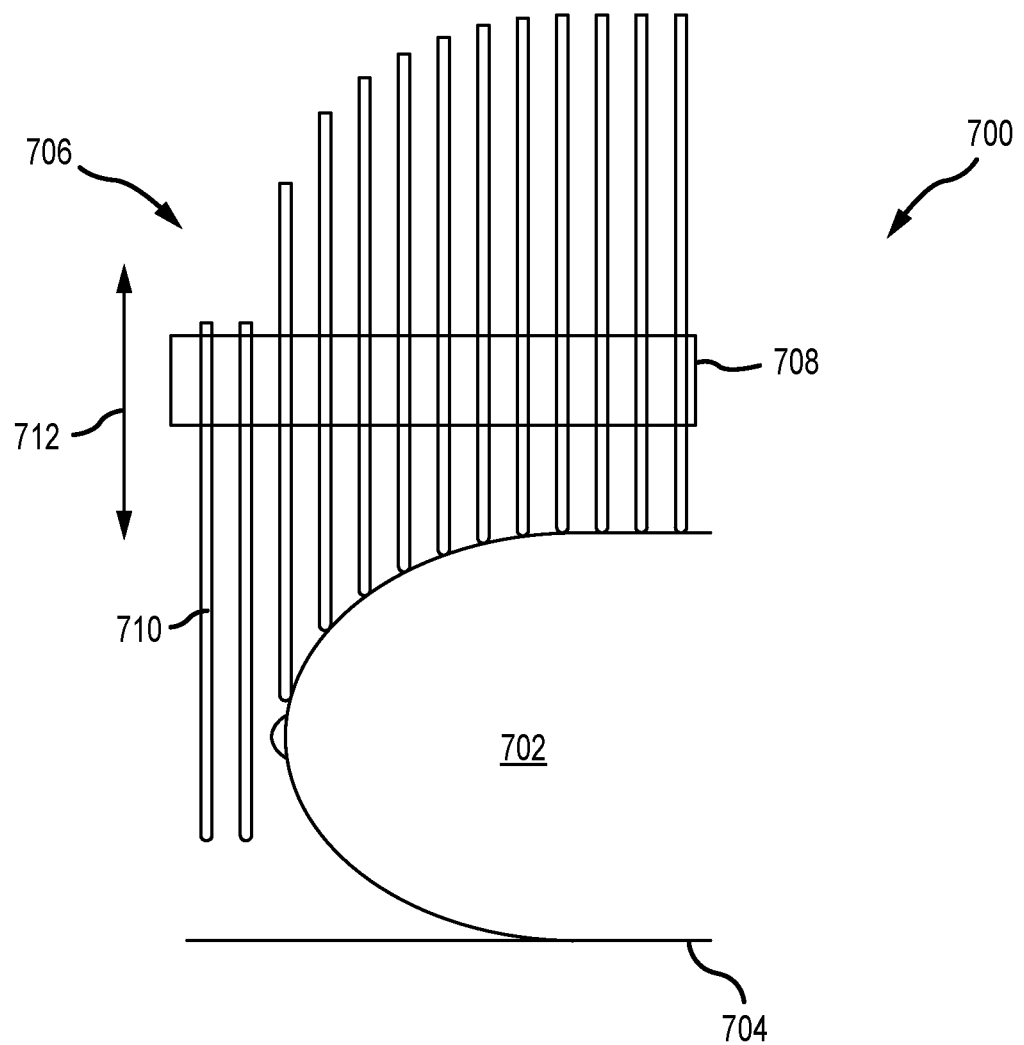
FIG. 7 is a schematic side view of another breast securement device.

FIG. 7 is a schematic side view of another breast securement device 700. The breast securement device 700 is configured to operationally couple to an imaging system (e.g., mammography, tomosynthesis, CT, ultrasound, MRI, etc.) and stabilize and/or shape a patient's breast 702 for image acquisitions. In this example, the breast securement device 700 includes a breast tray 704 configured to support the patient's breast 702. A paddle 706 is positioned above the breast tray 704 and is configured to move towards the breast tray 704 and contact at least a portion of the patient's breast 702. The paddle 706 enables the patient's breast 702 to be stabilized and/or shaped on the breast tray 704 so that the breast does not move during imaging and the patient's comfort level is increased.

In the example, the paddle 706 includes a substantially rigid frame 708 that supports an array of pins 710 moveable thereon. The pins 710 are configured to independently slide 712 within the paddle 706 and contour around the patient's breast 702. As such, the patient's breast 702 is stabilized between the paddle 706 and the breast tray 704 and the pins 710 are configured to create a relief of the patient's breast 702. The frame 708 does not contact and apply any compression force to the patient's breast 702. The pins 710 move 712 in a direction that is substantially similar to a direction of the movement of the paddle 706 so that the paddle 706 can contour to the patient's breast 702. In an aspect, each pin 710 may be formed from a radiolucent plastic so as to reduce or eliminate image artifacts. In other aspects, each pin 710 may be formed from a fiber optic pin.

Figure 8:
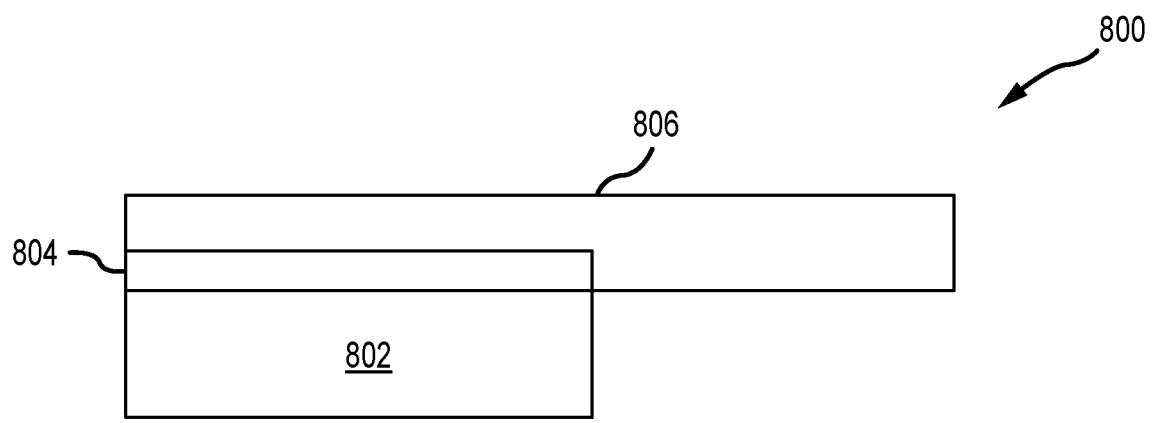
FIG. 8 is a schematic side view of another breast securement device.

FIG. 8 is a schematic side view of another breast securement device 800. The breast securement device 800 is configured to operationally couple to an imaging system (e.g., mammography, tomosynthesis, CT, ultrasound, MRI, etc.) and stabilize and/or shape a patient's breast for image acquisitions. In this example, the breast securement device 800 includes a bladder 802 that is selectively positionable adjacent to at least a portion of the patient's breast. The bladder 802 includes a non-Newtonian fluid disposed therein. The non-Newtonian fluid can be a shear thickening (e.g., dilatant) fluid that the viscosity of the fluid increases with increased stress, or a rheopecty fluid that the viscosity of the fluid increases with a duration of stress. As such, upon an application of a stress to the non-Newtonian fluid, the bladder 802 enables the patient's breast to be stabilized and/or shaped so that the breast does not move during imaging and the patient's comfort level is increased.

In the example, the breast securement device 800 includes an ultrasound generator 804 that is configured to apply stress towards the non-Newtonian fluid. In other examples, the generator can be a piezo transducer. The bladder 802 can be coupled to a paddle 806 so that the bladder 802 can be selectively positioned at least partially on the patient's breast. The bladder 802 and the non-Newtonian fluid may be radiolucent so that image artifacts are reduced or eliminated. In operation, the bladder 802 may be positioned relative to the patient's breast with the fluid therein being sufficiently motile (e.g., low viscosity) so that the bladder 802 can contour around at least a portion of the patient's breast. Stress can then be introduced to the non-Newtonian fluid so that the viscosity of the fluid increases and the bladder 802 stiffens so as to reduce or eliminate breast movement and to increase patient comfort.

The breast securement devices described in FIGS. 6-9, all use a paddle that contours at least partially around the patient's beast to stabilize and/or shape the patient's breast. These paddles, however, do not fully compress the patient's breast. Rather, the paddles restrict or prevent the patient's breast from moving during imaging procedures to reduce or eliminate image blurring, while increasing the efficiency, comfort, and performance of the imaging procedure. The paddles and components thereon can be substantially radiolucent or sonolucent so as to reduce or eliminate image artifacts from the paddle in the imaging.

This disclosure describes some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art. Any number of the features of the different examples described herein may be combined into one single example and alternate examples having fewer than or more than all of the features herein described are possible. It is to be understood that terminology employed herein is used for the purpose of describing particular examples only and is not intended to be limiting. It must be noted that, as used in this specification, the singular forms "a," "an," and "the" include plural referents unless the context clearly dictates otherwise.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. An imaging system for a breast, the imaging system comprising:
   a tube head;
   an x-ray source disposed in the tube head;
   an x-ray detector supported by a support structure; and
   a breast support device coupled to a front face of the support structure and disposed between the x-ray source and the x-ray detector, wherein the breast support device comprises a sling coupled to a supporting element for at least partially supporting the breast from below while on the breast support device, wherein the supporting element includes at least one support arm having a proximal end and a distal end, the proximal end is coupled to the front face such that the distal end extends from the front face along an axis that is orthogonal to the front face, the distal end coupled to the sling and the at least one support arm is moveable along the axis such that the sling selectively moves towards and away from the front face of the support structure.

2. The imaging system of claim 1, wherein the x-ray detector is disposed below a platform, and wherein the breast support device is disposed above the platform.

3. The imaging system of claim 2, wherein the platform comprises a flat upper surface, and wherein the sling has an upper surface that is concave in shape to support the breast.

4. The imaging system of claim 3, wherein the at least one support arm comprises a pair of support arms, and wherein the sling spans the pair of support arms.

5. The imaging system of claim 2, wherein the sling comprises a fabric.

6. The imaging system of claim 5, wherein the fabric is in contact with the supporting element that maintains the fabric in a position spaced apart from the platform.

7. The imaging system of claim 6, wherein the supporting element is more rigid than the sling.

8. The imaging system of claim 5, wherein the fabric is removably attached to the supporting element.

9. The imaging system of claim 5, wherein the fabric is configured to pull the breast into an imaging area.

10. The imaging system of claim 2, wherein the breast support device supports a weight of the breast during imaging.

11. The imaging system of claim 2, wherein the breast support device is configured to lift the breast above the platform.

12. The imaging system of claim 1, wherein the sling is configured to contour a lower surface of the breast.

13. The imaging system of claim 1, wherein at least a portion of the breast support device is removable.

14. The imaging system of claim 13, wherein the removable portion comprises a fabric.

15. The imaging system of claim 1, wherein an upper surface of the breast is not compressed when supported by the breast support device during imaging.

16. A method of imaging a breast with an imaging system comprising an x-ray source and an x-ray detector, the method comprising:
receiving the breast on a sling coupled to a supporting element including at least one support arm extending from a front face of a support structure of the imaging system, wherein the sling is disposed above the x-ray detector on a distal end of the at least one support arm, and a proximal end of the at least one support arm is coupled to the front face;
pulling the breast away from a chest wall by moving the at least one support arm having the sling along an axis that is orthogonal to the front face and in a direction towards the front face of the support structure;
maintaining a curvature of a lower portion of the breast with the sling;
while maintaining the curvature, emitting x-ray energy from the x-ray source towards the breast; and
while maintaining the curvature, receiving the x-ray energy at the x-ray detector.

17. The method of claim 16, further comprising, after receiving the breast, adjusting a shape of the lower portion of the breast.

18. The method of claim 16, wherein adjusting a shape of the breast comprises moving at least a portion of the sling.

* * * * *